US009676564B2

(12) United States Patent
Kawahara et al.

(10) Patent No.: US 9,676,564 B2
(45) Date of Patent: Jun. 13, 2017

(54) CONVEYANCE SYSTEM AND SYSTEM FOR INSPECTING ARTICLE TO BE CONVEYED

(71) Applicant: Bosch Packaging Technology K.K., Tokyo (JP)

(72) Inventors: Taiko Kawahara, Saitama (JP); Katsumi Shimizu, Saitama (JP)

(73) Assignee: Bosch Packaging Technology K.K., Tokyo (JP)

( * ) Notice: Subject to any disclaimer, the term of this patent is extended or adjusted under 35 U.S.C. 154(b) by 0 days.

(21) Appl. No.: 15/126,531

(22) PCT Filed: Mar. 13, 2015

(86) PCT No.: PCT/JP2015/057451
§ 371 (c)(1),
(2) Date: Sep. 15, 2016

(87) PCT Pub. No.: WO2015/146628
PCT Pub. Date: Oct. 1, 2015

(65) Prior Publication Data
US 2017/0088366 A1    Mar. 30, 2017

(30) Foreign Application Priority Data
Mar. 24, 2014    (JP) ................. 2014-059726

(51) Int. Cl.
*B65G 47/244*    (2006.01)
*B65G 47/84*    (2006.01)
*B65G 15/00*    (2006.01)

(52) U.S. Cl.
CPC ........... *B65G 47/846* (2013.01); *B65G 15/00* (2013.01)

(58) Field of Classification Search
CPC .... B65G 29/00; B65G 47/846; B65G 47/244; B65G 47/252; B65G 2201/0244; B65G 2201/02
USPC .. 198/375, 377.02, 379, 478.1, 480.1, 481.1
See application file for complete search history.

(56) References Cited

U.S. PATENT DOCUMENTS 2,822,943 A * 2/1958 Fedorchak ........... G01B 5/0002
                                                      198/379
2,927,679 A * 3/1960 Rively ..................... H01K 3/10
                                                      198/375
4,280,612 A * 7/1981 Nagano .................. B65C 9/065
                                                      198/379

(Continued)

FOREIGN PATENT DOCUMENTS

EP    1298428 A1    4/2003
JP    5667229        6/1981

(Continued)

OTHER PUBLICATIONS

International Search Report for Application No. PCT/JP2015/057451 dated Jun. 4, 2015 (English Translation, 2 pages).

*Primary Examiner* — James R Bidwell
(74) *Attorney, Agent, or Firm* — Michael Best & Friedrich LLP

(57) ABSTRACT

A conveyance system (1) and a system for inspecting an article to be conveyed by using the conveyance system (1) are provided with a purpose of preventing contact of an article to be conveyed with a guide with a simple structure, the conveyance system (1) including: a rotor section (2); a rotation mechanism (3); a pack (5); and a lift mechanism (4).

13 Claims, 15 Drawing Sheets

(56) References Cited

U.S. PATENT DOCUMENTS

| | | | |
|---|---|---|---|
| 4,395,300 A | 7/1983 | Hoffmann | |
| 4,471,644 A * | 9/1984 | Kimbell | B21D 22/08 29/563 |
| 4,697,688 A * | 10/1987 | Kimbell | B21D 22/08 198/346.2 |
| 5,137,136 A * | 8/1992 | Humele | B65C 9/065 156/567 |
| 5,150,782 A * | 9/1992 | Richter | B65C 9/065 198/379 |
| 5,205,392 A | 4/1993 | von Seld | |
| 7,328,784 B2 * | 2/2008 | Schinelli | B65C 9/04 198/379 |
| 7,921,980 B2 * | 4/2011 | Eder | B65C 3/16 198/377.01 |
| 2009/0301840 A1 * | 12/2009 | Lanfranchi | B65G 47/1457 198/379 |
| 2011/0253506 A1 * | 10/2011 | Kramer | B65C 9/06 198/379 |

FOREIGN PATENT DOCUMENTS

| | | |
|---|---|---|
| JP | 0442120 | 4/1992 |
| JP | 5294438 | 11/1993 |
| JP | 11100119 | 4/1999 |
| JP | 201019804 | 1/2010 |
| JP | 2012117900 | 6/2012 |
| JP | 2012202767 | 10/2012 |

\* cited by examiner

CONVEYANCE SYSTEM AND SYSTEM FOR INSPECTING ARTICLE TO BE CONVEYED

BACKGROUND OF THE INVENTION

The invention relates to a conveyance system for conveying a container and the like and to a technical field of a system for inspecting an article to be conveyed, the system inspecting damage to the container or presence of a foreign object and the like in the container.

It has conventionally been disclosed that a conveyance system for conveying a container is used for a device for performing inspection of the container and the like (see JP-A-2012-202767).

SUMMARY OF THE INVENTION

However, in the conveyance system as described in JP-A-2012-202767, the container comes in contact with a guide or the like, which possibly results in a scratch on an outer periphery of the container or damage to the container.

The invention has been made in view of such a circumstance and therefore has a purpose of providing a conveyance system and a system for inspecting an article to be conveyed that prevent contact of the article to be conveyed with a guide or the like with simple structures.

In order to solve the above-described problems, a conveyance system according to an embodiment of the invention includes, in the conveyance system for conveying an article to be conveyed: a rotor section having a disc-shaped rotor body that is rotatable about a first axis and a table that integrally rotates at an outer peripheral edge of the rotor body; a rotation mechanism having a rotary drive section that is mounted in the table and a transmission section that transmits rotary drive power for driving the rotary drive section; a pack having a first pack member that can accommodate the article to be conveyed in an upper portion, a second pack member that contacts an inner periphery of the first pack member in a vertically movable manner and in a lower portion of which the transmission section is inserted, and a pusher member that contacts an inner periphery of the second pack member in the vertically movable manner and on which the article to be conveyed is placed, and being rotatable about a second axis by the rotation mechanism; and a lift mechanism having an arm, one end of which is supported by the rotor body in a vertically movable manner, and the other end of which is used to place the first pack member thereon and supports the second pack member.

In addition, in the conveyance system according to the embodiment of the invention, the pack can be changed to a first state where at least a portion of the article to be conveyed is inserted in the first pack member and a second state where the arm moves downward, the second pack member and the first pack member thereby move downward, and the article to be conveyed that is placed on the pusher member is projected above the first pack member and the second pack member.

In addition, the conveyance system according to the embodiment of the invention is characterized by including a cap that presses the article to be conveyed from above in a manner to allow rotation thereof and that can move vertically in conjunction with vertical movement of the article to be conveyed.

In addition, the conveyance system according to the embodiment of the invention is characterized that the pusher member has a projected section that is radially projected and hangs on the second pack member from above.

In addition, the conveyance system according to the embodiment of the invention is characterized that the second pack member has a stopper section that receives the first pack member from below.

In addition, the conveyance system according to the embodiment of the invention is characterized that the lift mechanism has: a coupling member coupled to the arm; a cam follower supported by the coupling member; and a non-rotational cam member formed with a cam surface that abuts against the cam follower.

In addition, the conveyance system according to the embodiment of the invention is characterized that the transmission section has: a first transmission section on which the pusher is placed and that can move in a vertical direction; and a second transmission section that can only rotate, and the rotation mechanism has a vertical drive section that causes the first transmission section to move in the vertical direction.

In addition, the conveyance system according to the embodiment of the invention is characterized that the pack can be changed to a third state where the pusher member moves downward by the vertical drive section and the article to be conveyed is placed on the second pack member and the pusher member.

In addition, a system for inspecting an article to be conveyed according to the embodiment of the invention is characterized by including: a supply section for supplying the article to be conveyed; a supply rotor for placing the article to be conveyed supplied from the supply section on the pack; the conveyance system for conveying the article to be conveyed that has been supplied from the supply rotor and placed on the pack; an imaging device for taking an image of the article to be conveyed on the pack; and an inspecting section for inspecting the article to be conveyed from the image taken by the imaging device.

In addition, the system for inspecting an article to be conveyed according to the embodiment of the invention is characterized that the pack is brought into the second state or the third state at a position where the pack opposes the imaging device.

In addition, the system for inspecting an article to be conveyed according to the embodiment of the invention is characterized by having a pack cartridge in which the packs are aligned and a pack supply rotor to which the packs are supplied from the pack cartridge.

In addition, the system for inspecting an article to be conveyed according to the embodiment of the invention is characterized that the pack cartridge has a belt conveyor for conveying the pack.

The conveyance system according to the embodiment of the invention includes, in the conveyance system for conveying the article to be conveyed: the rotor section having the disc-shaped rotor body that is rotatable about the first axis and the table that integrally rotates at the outer peripheral edge of the rotor body; the rotation mechanism having the rotary drive section that is mounted in the table and the transmission section that transmits the rotary drive power for driving the rotary drive section; the pack having the first pack member that can accommodate the article to be conveyed in the upper portion, the second pack member that contacts the inner periphery of the first pack member in the vertically movable manner and in the lower portion of which the transmission section is inserted, and the pusher member that contacts the inner periphery of the second pack member in the vertically movable manner and on which the article to be conveyed is placed, and being rotatable about the second axis by the rotation mechanism; and the lift mechanism having the arm, the one end of which is supported by the rotor body in the vertically movable manner, and the other end of which is used to place the first pack member thereon and supports the second pack member. Thus, it is possible with a simple structure to prevent contact of the article to be conveyed with the guide or the like.

In addition, in the conveyance system according to the embodiment of the invention, the pack can be changed to the first state where at least the portion of the article to be conveyed is inserted in the first pack member and the second state where the arm moves downward, the second pack member and the first pack member thereby move downward, and the article to be conveyed that is placed on the pusher member is projected above the first pack member and the second pack member. Thus, the state can be changed in accordance with a situation.

In addition, the conveyance system according to the embodiment of the invention includes the cap that presses the article to be conveyed from above in the manner to allow rotation thereof and that can move vertically in conjunction with the vertical movement of the article to be conveyed. Thus, the article to be conveyed can stably be held.

In addition, in the conveyance system according to the embodiment of the invention, the pusher member has the projected section that is radially projected and hangs on the second pack member from above. Thus, the article to be conveyed can further stably be held.

In addition, in the conveyance system according to the embodiment of the invention, the second pack member has the stopper section that receives the first pack member from below. Thus, falling of the first pack downward can be prevented.

In addition, in the conveyance system according to the embodiment of the invention, the lift mechanism has: the coupling member coupled to the arm; the cam follower supported by the coupling member; and the non-rotational cam member formed with the cam surface that abuts against the cam follower. Thus, the arm, the first pack member, and the second pack member can be lifted or lowered with the simple structure.

In addition, in the conveyance system according to the embodiment of the invention, the transmission section has: the first transmission section on which the pusher is placed and that can rotate and move in the vertical direction; and the second transmission section that can only rotate, and the rotation mechanism has the vertical drive section that causes the first transmission section to move in the vertical direction. Thus, the pusher can move in the vertical direction.

In addition, in the conveyance system according to the embodiment of the invention, the pack can be changed to the third state where the pusher member moves downward by the vertical drive section and the article to be conveyed is placed on the second pack member and the pusher member. Thus, the article to be conveyed can stably be held and can rotate at a high speed.

In addition, the system for inspecting an article to be conveyed according to the embodiment of the invention includes: the supply section for supplying the article to be conveyed; the supply rotor for placing the article to be conveyed supplied from the supply section on the pack; the conveyance system for conveying the article to be conveyed that has been supplied from the supply rotor and placed on the pack; the imaging device for taking the image of the article to be conveyed on the pack; and the inspecting section for inspecting the article to be conveyed from the image taken by the imaging device. Thus, the article to be conveyed can accurately be inspected.

In addition, in the system for conveying an article to be conveyed according to the embodiment of the invention, the pack is brought into the second state or the third state at the position where the pack opposes the imaging device. Thus, the article to be conveyed can further accurately be inspected.

In addition, the system for inspecting an article to be conveyed according to the embodiment of the invention has the pack cartridge in which the packs are aligned and the pack supply rotor to which the packs are supplied from the pack cartridge. Thus, the packs can promptly be supplied in a manner to correspond to the article to be conveyed in a different shape.

In addition, in the system for inspecting an article to be conveyed according to the embodiment of the invention, the pack cartridge has the belt conveyor for conveying the pack. Thus, the pack can further promptly be supplied.

DETAILED DESCRIPTION

A description will hereinafter be made on embodiments of the invention by using the drawings.

Figure 1:
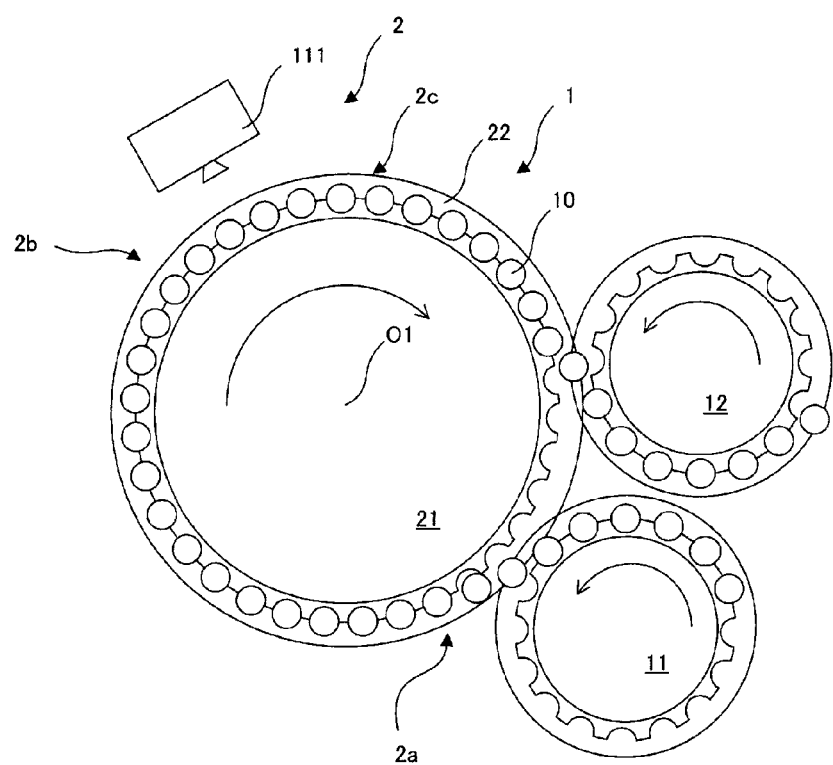
FIG. 1 is a plan view of a conveyance system of a first embodiment.
Figure 2:
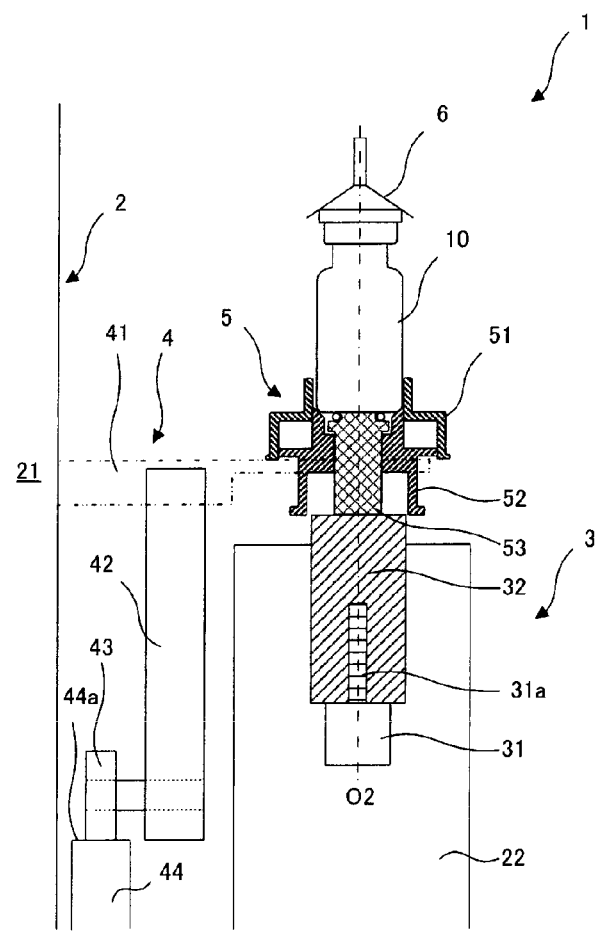
FIG. 2 is a view of a first state of the conveyance system of the first embodiment.
Figure 3:
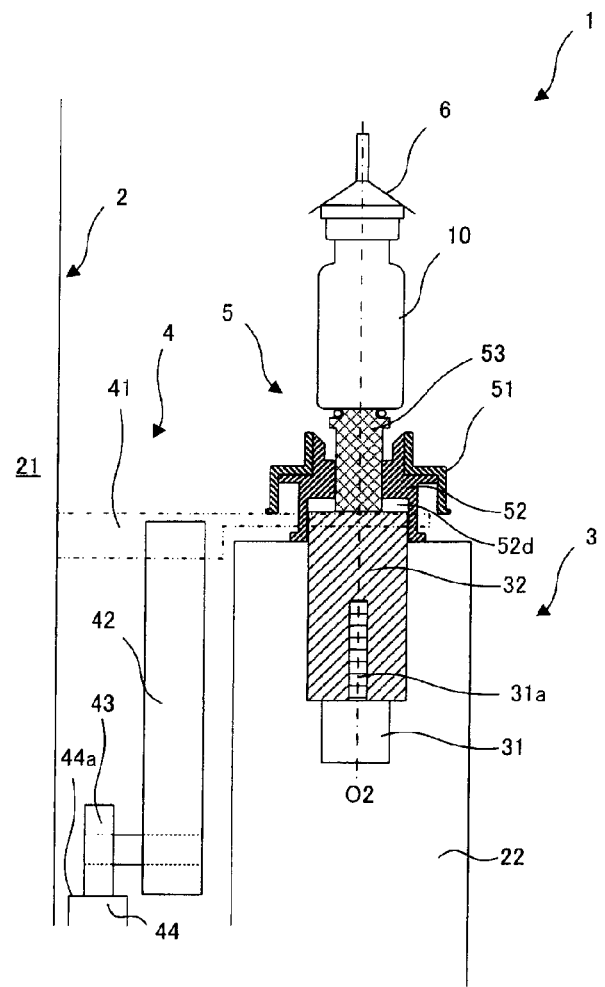
FIG. 3 is a view of a second state of the conveyance system of the first embodiment.

FIG. 1 is a plan view of a conveyance system 1 of a first embodiment. FIG. 2 is a view of a first state of the conveyance system of the first embodiment. FIG. 3 is a view of a second state of the conveyance system of the first embodiment.

The conveyance system 1 of this embodiment includes a rotor section 2, a rotation mechanism 3, a lift mechanism 4, a pack 5, and a cap 6. In the conveyance system 1 of this embodiment, an article to be conveyed 10 that is supported by the pack 5 and the cap 6 is conveyed in a state of being rotatable by the rotation mechanism 3 that is mounted at an outer peripheral edge of the rotor section 2 and in a state of being able to be lifted or lowered by the lift mechanism 4.

The rotor section 2 has: a substantially disc-shaped rotor body 21 that is rotatable about a first axis O1; and a table 22 that supports the rotation mechanism 3 at an outer peripheral edge of the rotor body 21. The rotor section 2 integrally rotates with the rotation mechanism 3, members of the lift mechanism 4 other than a cam member 44, the pack 5, and the cap 6.

The rotation mechanism 3 has: a rotary drive section 31 that includes a motor and the like mounted in the table 22; and a transmission section 32 that is coupled to an output shaft 31a of the rotary drive section 31 and transmits rotary drive power to the pack 5. Note that a bearing and the like, which are not depicted, are mounted between the table 22 and the transmission section 32.

The lift mechanism 4 has: an arm 41, one end of which is supported in a vertically movable manner with respect to the rotor body 21, and the other end of which is used to place a first pack member 51 thereon and supports a second pack member 52; a coupling member 42 that is coupled to the arm 41; a cam follower 43 that is supported by the coupling member 42; and the cam member 44 that is formed with a cam surface abutting against the cam follower 43 and is formed with a non-rotational cam surface 44a as a separate component from the rotor section 2.

The pack 5 has: the substantially cylindrical first pack member 51; the substantially cylindrical second pack member 52 that is fitted to an inner peripheral side of the first pack member 51 in a vertically movable manner; and a pusher member 53 that is fitted to an inner peripheral side of the second pack member 52 in a vertically movable manner and on which the article to be conveyed 10 is placed, and is rotatable about a second axis O2 by the rotation mechanism 3.

The first pack member 51 and the pusher member 53 are supported by the second pack member 52 from below and are assembled in a manner to be movable upward with respect to the second pack member 52. The second pack member 52 has a recess section 52d in a lower side thereof, in which the transmission section 32 is inserted. The pusher member 53 is placed on the transmission section 32 and is supported in a manner to be movable in a vertical direction within the second pack member 52.

The cap 6 presses the article to be conveyed 10 from above in a manner to allow rotation thereof and can move vertically in conjunction with vertical movement of the article to be conveyed 10.

Next, an operation of the conveyance system 1 in the first embodiment will be described. In the first embodiment, a case where the article to be conveyed 10 is inspected by an imaging device 110 will be described.

First, as depicted in FIG. 1, the article to be conveyed 10 is conveyed from an introducing rotor 11 to the rotor section 2 in a state of being placed on the pack 5. As depicted in FIG. 2, in the vicinity of a first region 2a of the rotor section 2, the article to be conveyed 10 is placed together with the pusher member 53 on the transmission section 32. In addition, the arm section 41 is located on an outer side of the second pack member 52 and supports the first pack member 51 from below. Accordingly, the first state where a lower portion of the article to be conveyed 10, which has been conveyed to the rotor section 2, is inserted in the first pack member 51 of the pack 5 is achieved. Thus, chances of contact of the article to be conveyed 10 with another part and of generation of a scratch thereon are reduced. In addition, the article to be conveyed 10 is stably supported by the pack 5.

However, in the first state, when it is attempted to take an image of the article to be conveyed 10 with the imaging device 110, the lower portion of the article to be conveyed 10 is covered with the first pack member 51, and thus the image thereof cannot be taken.

Accordingly, in the vicinity of a second region 2b before a position where the article to be conveyed 10 opposes the imaging device 110 depicted in FIG. 1, as depicted in FIG. 3, the cam follower 43 moves downward along the cam 44. Then, the coupling section 42 and the arm 41 move downward, the second pack member 52 and the first pack member 51 also move downward, and thereby the second state is achieved. At this time, by driving the rotary drive section 31, the output shaft 31a causes rotation of each of the transmission section 32, the second pack member 52, and the pusher member 53. Accordingly, the article to be conveyed 10 also rotates. Thus, a side and a portion of a bottom of the article to be conveyed 10 can be observed, and an image of the entire article to be conveyed 10 can accurately be captured by the imaging device 110.

Thereafter, in the vicinity of a third region 2c after the article to be conveyed 10 passes through the position where it opposes the imaging device 110 depicted in FIG. 1, as depicted in FIG. 2, the article to be conveyed 10, which has passed the imaging device 110, causes the cam follower 43 to move upward along the cam 44. Then, the coupling section 42 and the arm 41 move upward, the second pack member 52 and the first pack member 51 also move upward, and the first state depicted in FIG. 2 is achieved. Thereafter, the article to be conveyed 10 is discharged by a discharging rotor 12 as depicted in FIG. 1.

Just as described, in the conveyance system 1 of the first embodiment, the first pack member 51 and the second pack member 52 of the pack 5 move upward and guard the article to be conveyed 10 during conveyance of the article to be conveyed 10. In this way, the chances of contact of the article to be conveyed 10 with the other part and of generation of the scratch thereon are reduced, and the article to be conveyed 10 is stably supported by the pack 5. In addition, when it is necessary to observe the article to be conveyed 10 during imaging and the like, the first pack member 51 and the second pack member 52 of the pack 5 move downward, so as to allow the entire article to be conveyed 10 to be observed from the side. In this way, the entire article to be conveyed 10 can accurately be observed.

Next, a description will be made on a second embodiment.

Figure 4:
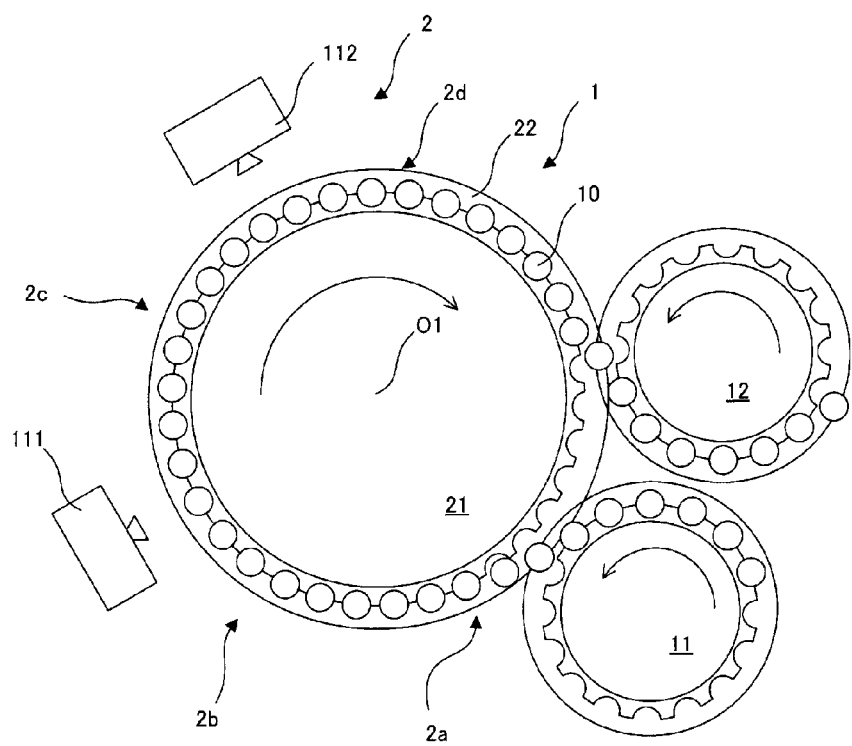
FIG. 4 is a plan view of a conveyance system of a second embodiment.
Figure 5:
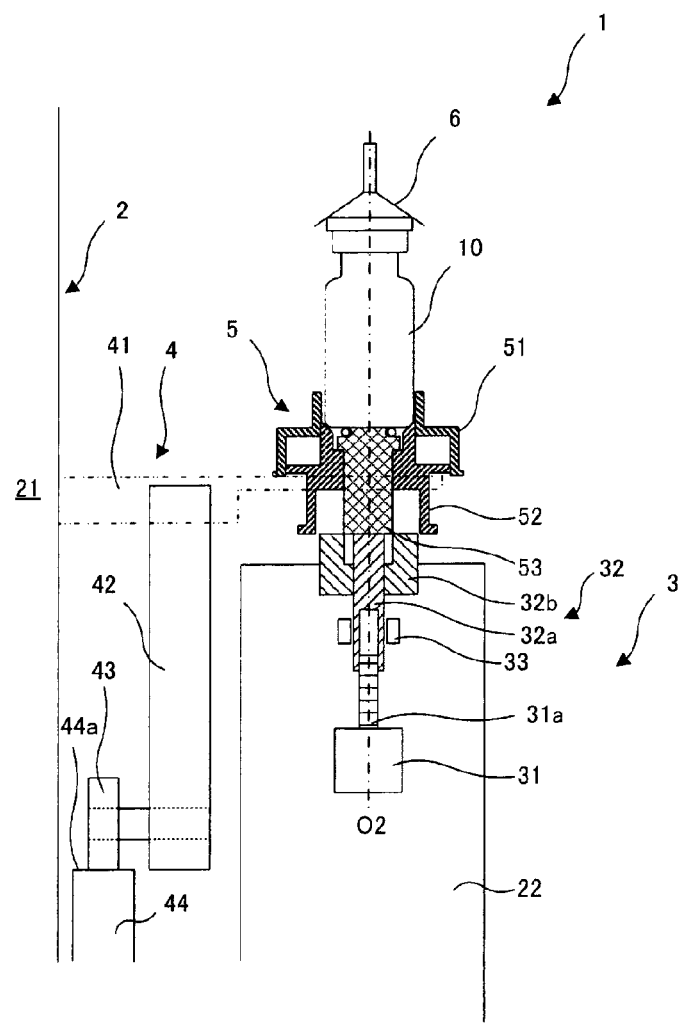
FIG. 5 is a view of a first state of the conveyance system of the second embodiment.
Figure 6:
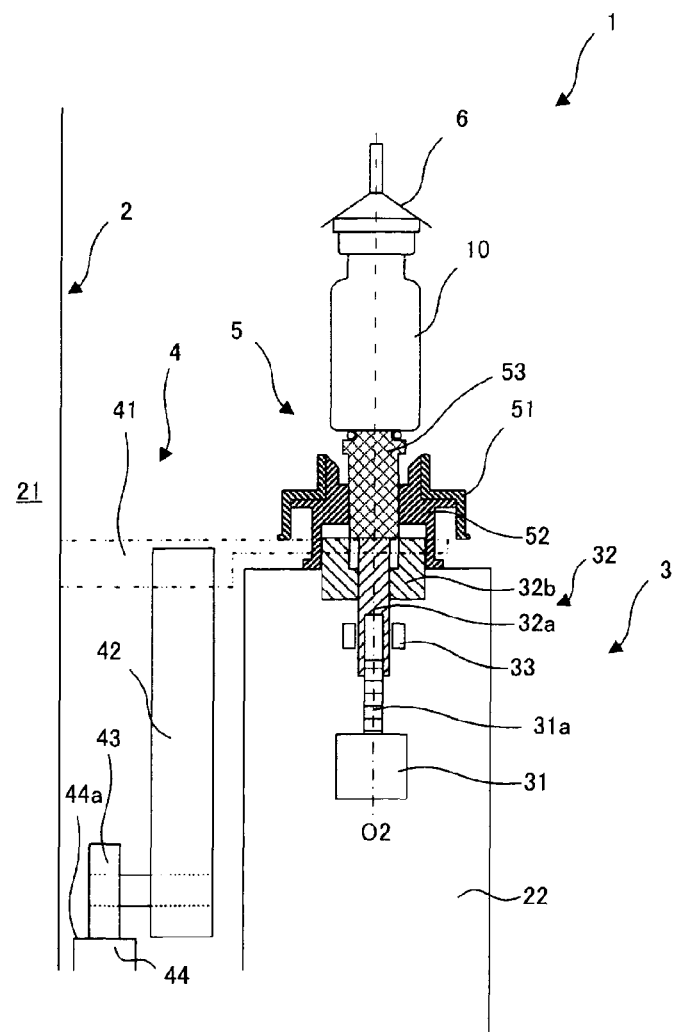
FIG. 6 is a view of a second state of the conveyance system of the second embodiment.
Figure 7:
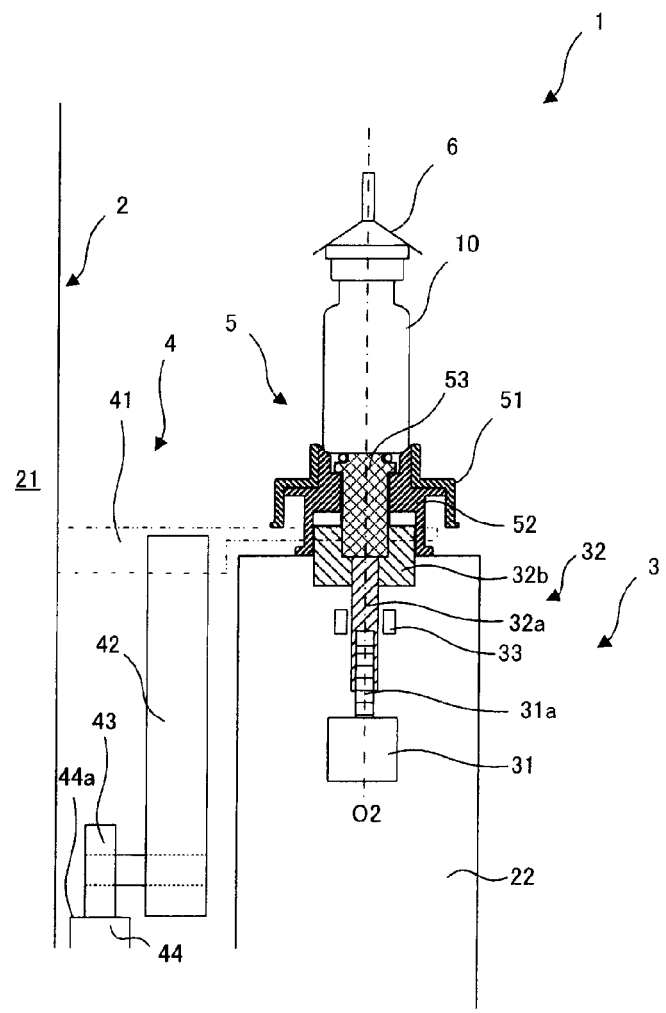
FIG. 7 is a view of a third state of the conveyance system of the second embodiment.

FIG. 4 is a plan view of a conveyance system of the second embodiment. FIG. 5 is a view of a first state of the conveyance system of the second embodiment. FIG. 6 is a view of a second state of the conveyance system of the second embodiment. FIG. 7 is a view of a third state of the conveyance system of the second embodiment.

The conveyance system 1 of the second embodiment has the article to be conveyed 10 as a container that contains a drug or the like, and, as depicted in FIG. 4, includes a first imaging device 110a that inspects external appearance and a second imaging device 110b that inspects for presence of a foreign object in the container. By the conveyance system 1 of the second embodiment, the article to be conveyed 10 is conveyed in a third state where it is inspected for the presence of the foreign object in the container, in addition to the first state during normal conveyance and the second state where it is inspected for the external appearance in the first embodiment.

Accordingly, instead of the conveyance system 1 of the first embodiment, in the conveyance system 1 of the second embodiment, as depicted in FIG. 5, the rotation mechanism 3 has: the transmission section 32 divided into a first transmission section 32a that can rotate and move in the vertical direction and a second transmission section 32b that can only rotate; and a vertical drive section 33 that causes the first transmission section 32a to move in the vertical direction.

The first transmission section 32a is coupled to the output shaft 31a of the rotary drive section 31 by a spline and the like in a manner to integrally rotate therewith and be movable in the vertical direction. The first transmission section 32a is also coupled to the second transmission section 32b by a spline and the like in a manner to integrally rotate therewith and be movable in the vertical direction. The pusher member 53 is placed on the first transmission section 32a. The second transmission section 32b receives the rotary drive power that is transmitted from the first transmission section 32a, and thereby rotates. A bearing and the like, which are not depicted, are mounted between table 22 and each of the output shaft 31a of the drive section 31, the first transmission section 32a, and the second transmission section 32b.

The vertical drive section 33 causes the first transmission section 32a to move in the vertical direction. The vertical drive section 33 may be an actuator such as a linear motor or a solenoid, for example.

Next, an operation of the conveyance system 1 in the second embodiment will be described. In the second embodiment, a case where the article to be conveyed 10 is inspected by the first imaging device 110a and the second imaging device 110b will be described.

First, as depicted in FIG. 4, the article to be conveyed 10 is conveyed from the introducing rotor 11 to the rotor section 2 in a state of being placed on the pack 5. In the vicinity of the first region 2a of the rotor section 2, as depicted in FIG. 5, the article to be conveyed 10 is placed together with the pusher member 53 on the transmission section 32. In addition, the arm section 41 is located on the outer side of the second pack member 52 and supports the first pack member 51 from below. Accordingly, the first state where the lower portion of the article to be conveyed 10, which has been conveyed to the rotor section 2, is inserted in the first pack member 51 of the pack 5 is achieved. Thus, the chances of contact of the article to be conveyed 10 with the other part and of generation of the scratch thereon are reduced. In addition, the article to be conveyed 10 is stably supported by the pack 5.

However, in the first state, when it is attempted to take the image of the article to be conveyed 10 with the first imaging device 110, the lower portion of the article to be conveyed 10 is covered with the first pack member 51, and thus the image thereof cannot be taken.

Accordingly, in the vicinity of the second region 2b before the position where the article to be conveyed 10 opposes the first imaging device 110a depicted in FIG. 4, as depicted in FIG. 6, the cam follower 43 moves downward along the cam 44. Then, the coupling section 42 and the arm 41 move downward, the second pack member 52 and the first pack member 51 also move downward, and thereby the second state is achieved. At this time, by driving the rotary drive section 31, the output shaft 31a causes rotation of each of the transmission section 32, the second pack member 52, and the pusher member 53. Accordingly, the article to be conveyed 10 also rotates. Thus, a front side portion and the portion of the bottom of the article to be conveyed 10 can be observed, and the image of the entire article to be conveyed 10 can accurately be taken by the first imaging device 1110a.

Thereafter, in the vicinity of the third region 2c that is before the article to be conveyed 10 arrives at a position where it opposes the second imaging device 110b, as depicted in FIG. 7, the article to be conveyed 10, which has passed the first imaging device 110a, drives the vertical drive section 33 and causes the first transmission section 32a to move downward. Then, the pusher member 53 moves downward, the article to be conveyed 10 also moves downward, and the third state is achieved. At this time, it is set such that the cap 6 also moves downward. At this time, the first transmission section 32a, the second transmission section 32b, and the pusher member 53 keep rotating due to driving of the drive section 31, and the article to be conveyed 10 thereby rotates.

The second imaging device 110b is used to inspect for the presence of the foreign object in the container as the article to be conveyed 10. Accordingly, in order to make the foreign object spread in the container, a rotational frequency of the article to be conveyed 10 at a time of being inspected by the second imaging device 110b is preferably set higher than that at a time when the external appearance thereof is inspected by the first imaging device 110a. In addition, in order to stably hold the article to be conveyed 10 during high-speed rotation, the lower portion of the article to be conveyed 10 is preferably partially supported by the first pack member 51 and the second pack member 52. In the conveyance system 1 of the second embodiment, even when the lower portion of the article to be conveyed 10 is partially supported by the first pack member 51 and the second pack member 52, the foreign object in the article to be conveyed 10 is spread upward by the rotation. Thus, an image of the foreign object can be taken by the second imaging device 110b for the inspection.

Thereafter, in the vicinity of a fourth region 2d depicted in FIG. 7, the article to be conveyed 10, which has passed the second imaging device 112, causes the cam follower 43 to move upward along the cam 44. Then, the coupling section 42 and the arm 41 move upward, the second pack member 52 and the first pack member 51 also move upward, and the first state depicted in FIG. 5 is achieved. Thereafter, the article to be conveyed 10 is discharged by the discharging rotor 12 as depicted in FIG. 4.

As described above, in the conveyance system 1 of the second embodiment, the first pack member 51 and the second pack member 52 of the pack 5 move upward and guard the article to be conveyed 10 during the conveyance of the article to be conveyed 10. In this way, the chances of contact of the article to be conveyed 10 with the other part and of generation of the scratch thereon are reduced, and the article to be conveyed 10 is stably be supported by the pack 5. In addition, when it is necessary to observe the article to be conveyed 10 during the imaging and the like, the first pack member 51 and the second pack member 52 of the pack 5 move downward, so as to allow the entire article to be conveyed 10 to be observed from the side. In this way, the entire article to be conveyed 10 can accurately be observed. Furthermore, the first transmission section 32a is coupled to the output shaft 31a of the rotary drive section 31 by the spline and the like in the manner to integrally rotate therewith and be movable in the vertical direction, and is also coupled to the second transmission section 32b by the spline and the like in the manner to integrally rotate therewith and be movable in the vertical direction. Thus, the stable high-speed rotation of the entire article to be conveyed 10 can be realized while the lower portion thereof is partially held by the first pack member 51 and the second pack member 52 of the pack 5.

Next, the pack 5 will specifically be described. First, a description will be made on a first pack 5a that is suited for a first article to be conveyed 10a.

Figure 8C:
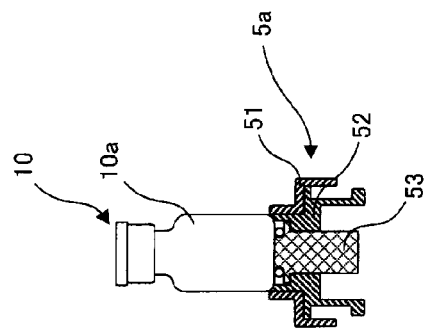
FIGS. 8(a), 8(b) and 8(c) are views of a first pack that is suited for a first article to be conveyed.
Figure 8B:
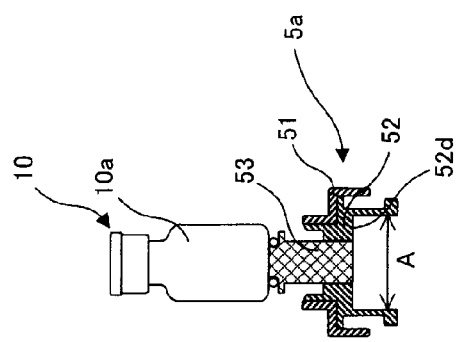

FIG. 8 includes views of the first pack 5a that is suited for the first article to be conveyed 10a. FIG. 9 includes views of a second pack 5b that is suited for a second article to be conveyed 10b. Note that, in each drawing, (a) depicts the first state, (b) depicts the second state, and (c) depicts the third state.

The first pack 5a that is depicted in FIG. 8 has the first pack member 51, the second pack member 52, and the pusher member 53.

The first pack member 51 has: a first cylindrical section 51a that has an inner diameter for accommodating the first article to be conveyed 10a; a second cylindrical section 51b that has a different diameter from the first cylindrical section 51a; a step section 51c that couples the first cylindrical section 51a and the second cylindrical section 51b. The second pack member 52 has: an outer peripheral section 52a that contacts an inner periphery of the second cylindrical section 51b; an inner peripheral section 52b that contacts the pusher member 53; and a stopper section 52c that receives the step section 51c from below. In addition, the recess section 52d, in which the transmission section 32 as depicted in FIG. 6 is inserted, is formed below the inner peripheral section 52b. The pusher member 53 has: a columnar section 53a that contacts the inner peripheral section 52b; a projected section 53b that is radially projected from the columnar section 53a and hangs on the second pack member 52 from above; and a placement section 53c on which the first article to be conveyed 10a is placed.

Figure 8A:
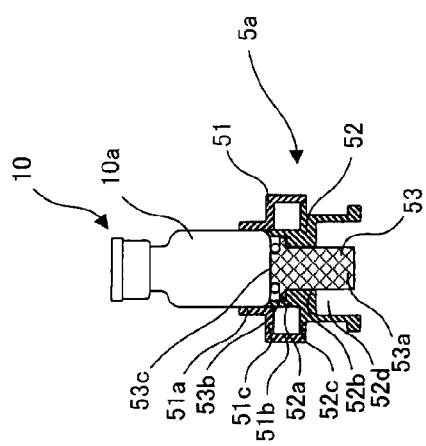
Figure 9C:
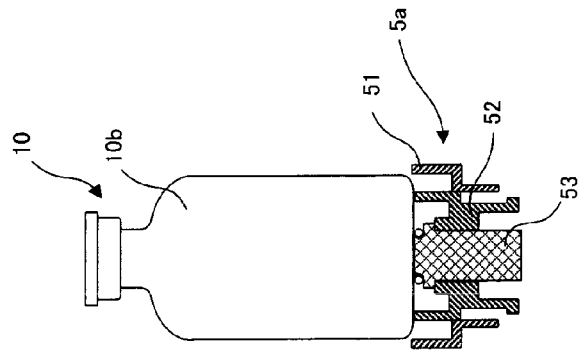
FIGS. 9(a), 9(b) and 9(c) are views of a second pack that is suited for a second article to be conveyed.

In the first state, as depicted in FIG. 8(a), the first article to be conveyed 10a is stably held because it is placed on the placement section 53c and is supported at a lateral surface by the first cylindrical section 51a. In the second state, because the arm 41 moves downward as depicted in FIG. 6, as depicted in FIG. 8(b), the first pack member 51 and the second pack member 52 move downward. Thus, the almost entire first article to be conveyed 10a that is placed on the pusher member 53 can be observed except for a bottom surface. In the third state, the pusher member 53 is lowered as depicted in FIG. 7, and the first article to be conveyed 10a is supported not only by the pusher member 53 but also by the second pack member 52. Thus, the first article to be conveyed 10a can stably be held even during the high-speed rotation.

Next, a description will be made on the second pack 5b that is suited for the larger second article to be conveyed 10b than the first article to be conveyed 10a.

The second pack 5b that is depicted in FIG. 9 has the first pack member 51, the second pack member 52, and the pusher member 53.

The first pack member 51 has: the first cylindrical section 51a that has an inner diameter for accommodating the second article to be conveyed 10b; the second cylindrical section 51b that has a different diameter from the first cylindrical section 51a; and the step section 51c that couples the first cylindrical section 51a and the second cylindrical section 51b. The second pack member 52 has: the outer peripheral section 52a that contacts the inner periphery of the second cylindrical section 51b; and the inner peripheral section 52b that contacts the pusher member 53. In addition, the recess section 52d, in which the transmission section 32 as depicted in FIG. 3 is inserted, is formed below the inner peripheral section 52b. The pusher member 53 has: the columnar section 53a that contacts the inner peripheral section 52b; the projected section 53b that is radially projected from the columnar section 53a and hangs on the second pack member 52 from above; and the placement section 53c on which the second article to be conveyed 10b is placed.

Figure 9B:
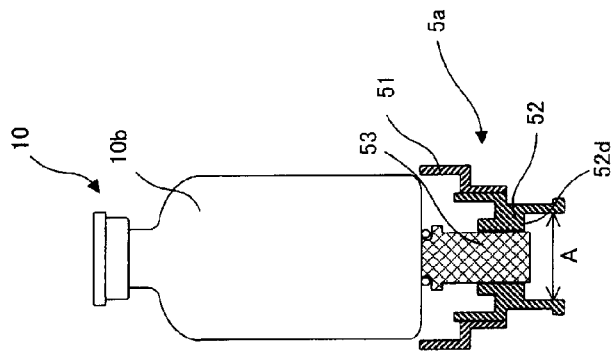
Figure 9A:
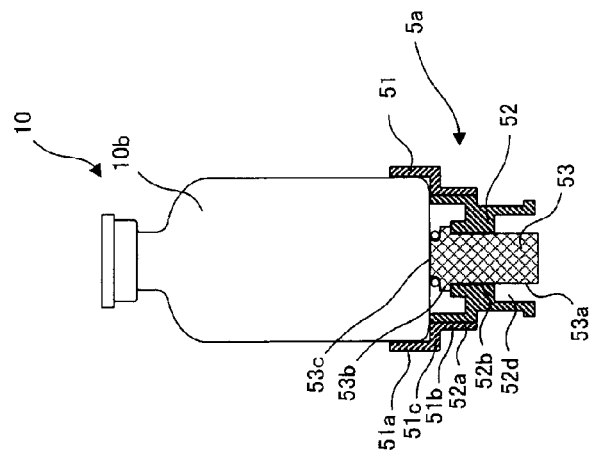

In the first state, as depicted in FIG. 9(a), the second article to be conveyed 10b is stably held because it is placed on the step section 51c and the placement section 53c and is supported at a side surface by the first cylindrical section 51a. In the second state, because the arm 41 moves downward as depicted in FIG. 6, as depicted in FIG. 9(b), the first pack member 51 and the second pack member 52 move downward. Thus, the almost entire second article to be conveyed 10b that is placed on the pusher member 53 can be observed except for a bottom surface. In the third state, the pusher member 53 is lowered as depicted in FIG. 7, and the second article to be conveyed 10b is supported not only by the pusher member 53 but also by the second pack member 52. Thus, the second article to be conveyed 10b can stably be held even during the high-speed rotation.

As described above, in the conveyance system 1 of this embodiment, plural types of the pack 5 can be provided in accordance with dimensions of the article to be conveyed 10. The different types of the pack 5 may have a similar structure, and only the dimension of an upper portion of the first pack member 51 may be changed in accordance with the article to be conveyed 10. In particular, the recess sections 52d that is located below the second pack members 52 and are depicted in FIG. 8(b) and FIG. 9(b) is preferably formed to have the same inner diameter. In addition, in the case of the conveyance system 1 of the second embodiment, diameters of the pusher members 53 are preferably the same.

In addition, in the conveyance system 1 of this embodiment, the recess sections 52d below the second pack members 52 are formed to have the same inner diameter. Thus, the transmission section 32 of the rotation mechanism 3 is accurately inserted in the recess section 52d of the second pack member 52. Furthermore, in the case of the conveyance system 1 of the second embodiment, the pusher members 53 are formed to have the same diameter. In this way, the pusher member 53 can accurately be inserted in the transmission section 32.

Figure 10B:
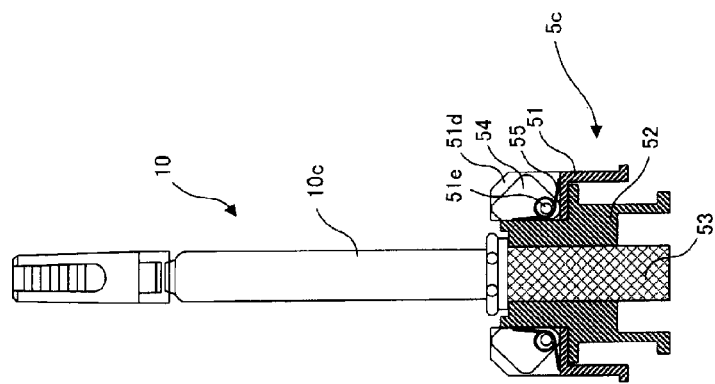
FIGS. 10(a) and 10(b) are views of a third pack in the case where a long object is used as an article to be conveyed.
Figure 10A:
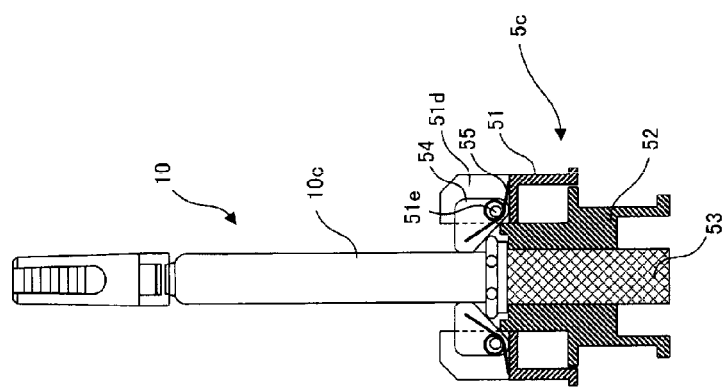

FIG. 10 includes views of a third pack 5c in the case where a long object is used as an article to be conveyed 10c. Note that FIG. 10(a) depicts the first state and FIG. 10(b) depicts the second state.

In an example in which the long object like a syringe as depicted in FIG. 10 is used as the article to be conveyed 10c, the third pack 5c preferably has a pressing member 54 and an urging member 55. The pressing member 54 is rotatably attached to a shaft 51e that is attached to a recess section 51d formed in the first pack member 51. The urging member 55 is attached to the shaft 51e and urges the pressing member 54 in a direction to close the pressing member 54 with respect to the first pack member 51. That is, the urging member 55 urges the pressing member 54 in a direction to press the article to be conveyed 10c.

As described above, even in the case where the article to be conveyed 10c that is the long object like the syringe is conveyed, the article to be conveyed 10c can stably be conveyed by using the pressing member 54 and the urging member 55.

Next, a description will be made on a system for inspecting an article to be conveyed that includes the conveyance system of this embodiment.

Figure 11:
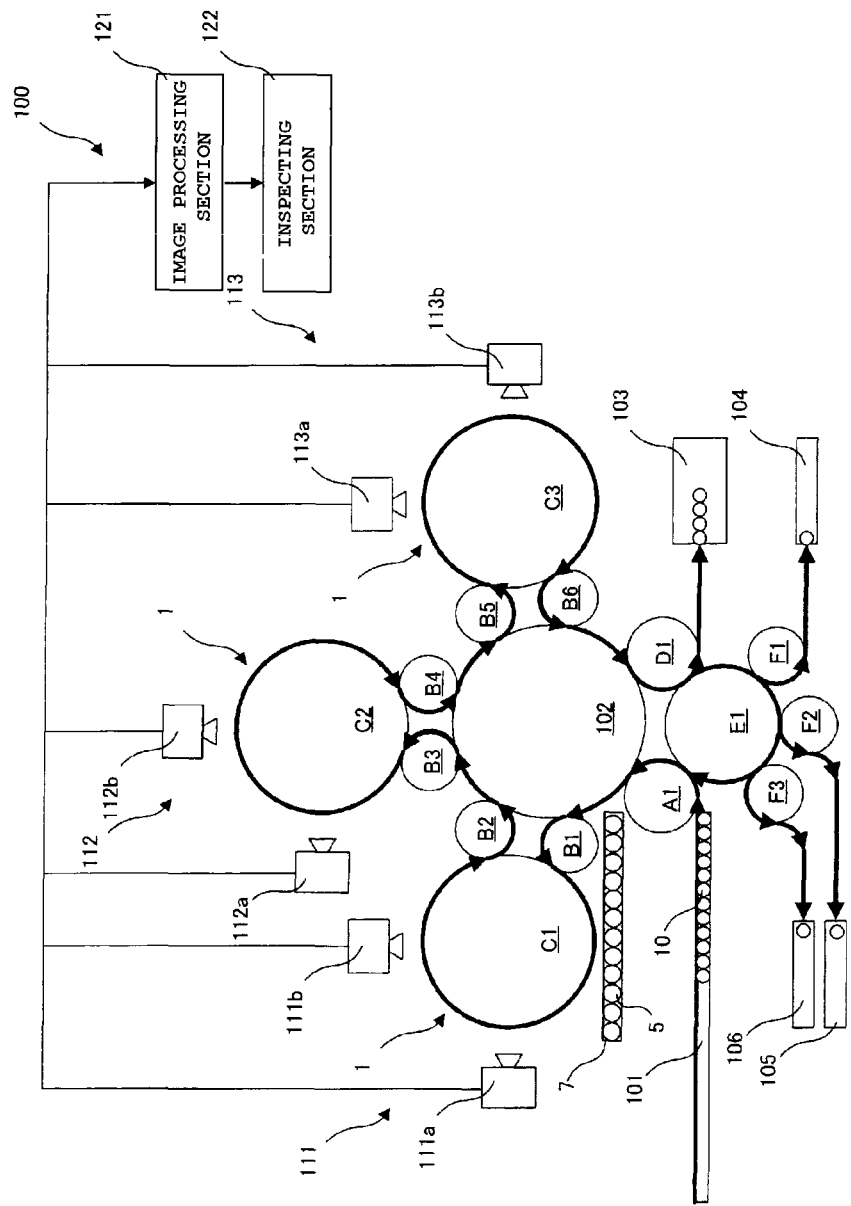
FIG. 11 is a view of a system for inspecting an article to be conveyed, the system including the conveyance system of this embodiment.

FIG. 11 is a view of the system for inspecting an article to be conveyed that includes the conveyance system of this embodiment.

A system for inspecting an article to be conveyed 100 that includes the conveyance system 1 of this embodiment includes: a supply section 101 for supplying the article to be conveyed 10; a supply rotor A1 for placing the article to be conveyed 10 supplied from the supply section 101 on the pack 5; the conveyance system 1 for conveying the article to be conveyed 10 that has been supplied from the supply rotor A1 and placed on the pack 5; imaging devices 111, 112, 113, each of which takes an image of the article to be conveyed 10 on the pack 5; an image processing section 121 for performing image processing on the image taken by each of the imaging devices 111, 112, 113; and an inspecting section 122 for inspecting the article to be conveyed 10 from the images that is processed by the image processing section 121.

First, in the system for inspecting an article to be conveyed 100 depicted in FIG. 11, the article to be conveyed 10 that is placed on the pack 5 depicted in FIG. 2 is supplied from the supply section 101. The supply section 101 may be constructed of a supply screw described in JP-A-2012-202767 or the like. The article to be conveyed 10 that has been supplied from the supply section 101 is placed on the pack 5 by the supply rotor A1 and is then conveyed to a central rotor 102. The article to be conveyed 10 that has been conveyed to the central rotor 102 is conveyed to a first inspecting rotor C1 through a first relay rotor B1, and images thereof are taken by a first imaging device 111a and a second imaging device 111b for inspection by the inspecting section 122. Thereafter, the article to be conveyed 10 returns to the central rotor 102 through a second relay rotor B2. In this case, it is preferred to switch between the first state and the second state or the third state by using the conveyance system 1 of this embodiment for the first inspecting rotor C1. Whether to select the second state or the third state only needs to be determined in accordance with contents of the inspection. Note that the first inspecting rotor C1, a second inspecting rotor C2, and a third inspecting rotor C3 each correspond to the conveyance system 1.

Note that, in this embodiment, the article to be conveyed 10 that is placed on the pack 5 is indirectly supplied from the supply rotor A1 to the first inspecting rotor C1 through the central rotor 102 and the first relay rotor B1; however, the article to be conveyed 10 may directly be conveyed from the supply rotor A1 to the first inspecting rotor C1.

Next, the article to be conveyed 10 that has been conveyed to the central rotor 102 is conveyed to the second inspecting rotor C2 through a third relay rotor B3, and the images thereof are taken by a third imaging device 111c and a fourth imaging device 111d for the inspection by the inspecting section 122. Thereafter, the article to be conveyed 10 returns to the central rotor 102 through a fourth relay rotor B4. Also, in the case of the second inspecting rotor C2, similar to the case of the first inspecting rotor C1, it is preferred to switch between the first state and the second state or the third state by using the conveyance system 1 of this embodiment. Whether to select the second state or the third state may be determined in accordance with the contents of the inspection.

Next, the article to be conveyed 10 that has been conveyed from the fourth relay rotor B4 to the central rotor 102 is conveyed to the third inspecting rotor C3 through a fifth relay rotor B5, the images thereof are taken by a fifth imaging device 111e and a sixth imaging device 111f for the inspection by the inspecting section 122. Thereafter, the article to be conveyed 10 returns to the central rotor 102 through a sixth relay rotor B6. Also, in the case of the third inspecting rotor C3, similar to the case of the first inspecting rotor C1 or the second inspecting rotor C2, it is preferred to switch between the first state and the second state or the third state by using the conveyance system 1 of this embodiment. Whether to select the second state or the third state may be determined in accordance with the contents of the inspection.

Next, the article to be conveyed 10 as a fine article that has been conveyed from the sixth relay rotor B6 to the central rotor 102 is conveyed to a shipment tray 103 through a discharge rotor Dl. Here, the article to be conveyed 10 that has been determined as a defective article by the inspecting section 122 is conveyed to a defective article relay rotor E1. The article to be conveyed 10 that has been determined as the defective article in the first inspecting rotor C1 is discharged from the defective article relay rotor E1 to a first defective article tray 104 through a first defective article discharge rotor F1. The article to be conveyed 10 that has been determined as the defective article in the second inspecting rotor C2 is discharged from the defective article relay rotor E1 to a second defective article tray 105 through a second defective article discharge rotor F2. The article to be conveyed 10 that has been determined as the defective article in the third inspecting rotor C3 is discharged from the defective article relay rotor E1 to a third defective article tray 106 through a third defective article discharge rotor F3.

As described above, in addition to operational effects of the conveyance system 1, plural types of the inspection on the article to be conveyed 10 can promptly and accurately be performed by using the conveyance system 1 for the system for inspecting an article to be conveyed 100.

Next, a description will be made on a pack cartridge 7 for the system for inspecting an article to be conveyed 100 of this embodiment. The system for inspecting an article to be conveyed 100 of this embodiment is configured that the pack 5 circulates through each of the rotors in advance and the article to be conveyed 10 is placed on the pack 5 at a time when the article to be conveyed 10 is supplied to the supply rotor A1. Conventionally, when containers in different sizes are conveyed, a large number of components in the conveyance system need to be exchanged in accordance with the size of the container, which requires significant workload and time.

In the system for inspecting an article to be conveyed 100 of this embodiment, as depicted in FIG. 8, FIG. 9, and FIG. 10, the pack 5 in the different size is used when the different article to be conveyed 10 is inspected. Because the different pack 5 is used, the pack 5 in the system for inspecting an article to be conveyed 100 needs to be exchanged.

Figure 12:
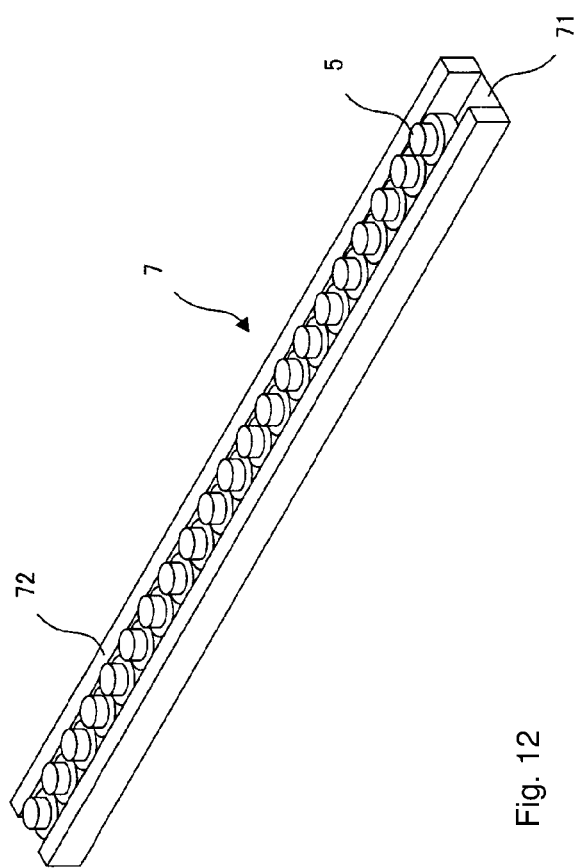
FIG. 12 is a view of a pack cartridge for the system for inspecting an article to be conveyed of this embodiment.
Figure 13:
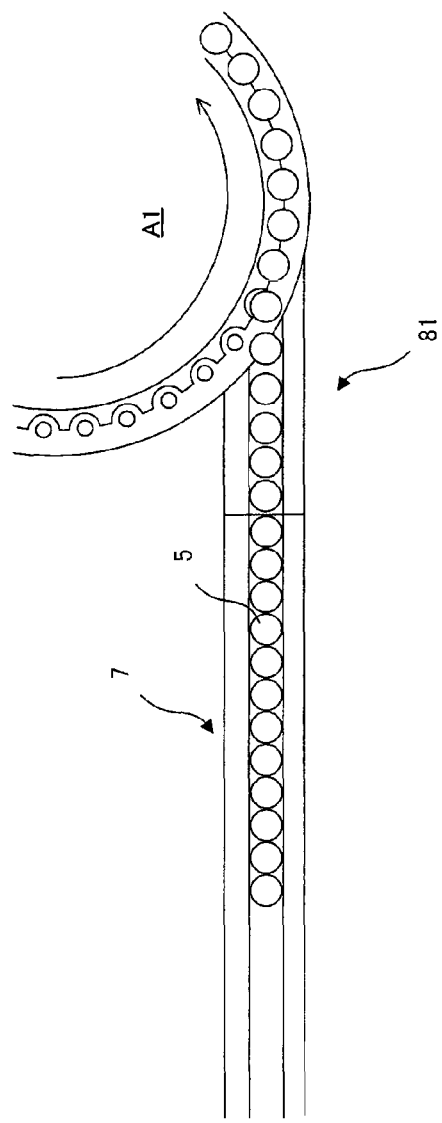
FIG. 13 is a view of a situation where packs are supplied from the pack cartridge to a supply rotor in the system for inspecting the article to be conveyed of this embodiment.
Figure 14:
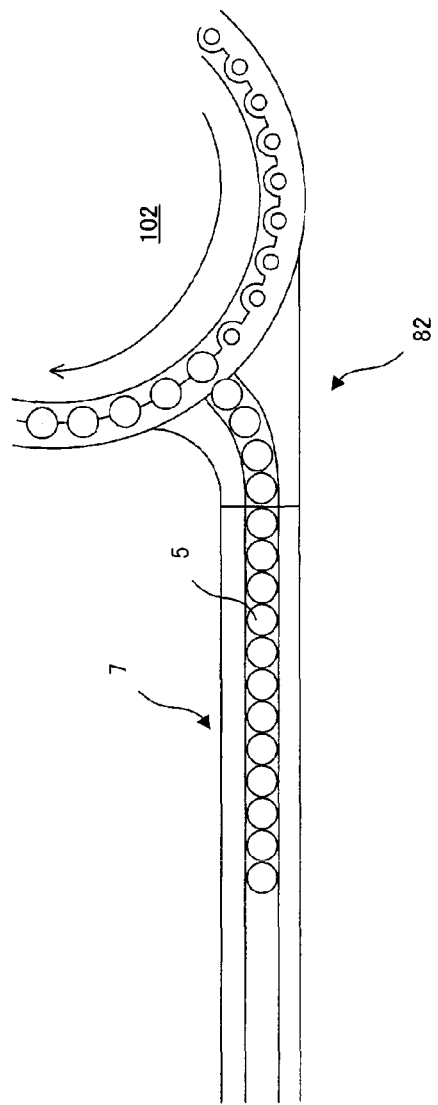
FIG. 14 is a view of a situation where the packs are supplied from the pack cartridge to a central rotor in the system for inspecting the article to be conveyed of this embodiment.

FIG. 12 is a view of the pack cartridge for the system for inspecting the article to be conveyed of this embodiment. FIG. 13 is a view of a situation where the packs are supplied from the pack cartridge to the supply rotor in the system for inspecting the article to be conveyed of this embodiment. FIG. 14 is a view of a situation where the packs are supplied from the pack cartridge to the central rotor in the system for inspecting the article to be conveyed of this embodiment.

As depicted in FIG. 12, the pack cartridge 7 for the system for inspecting an article to be conveyed 100 of this embodiment has: a bottom plate 71 that is formed to have a smooth surface; and side walls 72 that extend upward from both ends of the bottom plate 71 in a short direction. On the bottom plate 71 of the pack cartridge 7, the packs 5 are aligned in a longitudinal direction.

The cartridge 7, in which the packs 5 are aligned as described above, is coupled to the supply rotor A1 by a first adapter 81 as depicted in FIG. 13. The first adapter 81 feeds the packs 5 in the same direction as a direction in which the packs 5 are fed from the pack cartridge 7. Then, the packs 5 are sequentially supplied from the pack cartridge 7 to the supply rotor A1. In this case, the supply rotor A1 constitutes the pack supply rotor.

In addition, the pack cartridge 7 may be coupled to the central rotor 102 by a second adapter 82 as depicted in FIG. 14. The second adapter 82 feeds the packs 5 in a different direction from the direction in which the packs 5 are fed from the pack cartridge 7. Then, the packs 5 are sequentially supplied from the cartridge 7 to the central rotor 102. In this case, the central rotor 102 constitutes the pack supply rotor.

As described above, by using the cartridge 7 in which the packs 5 are aligned, the packs 5 can smoothly be exchanged in a short time period.

Figure 15:
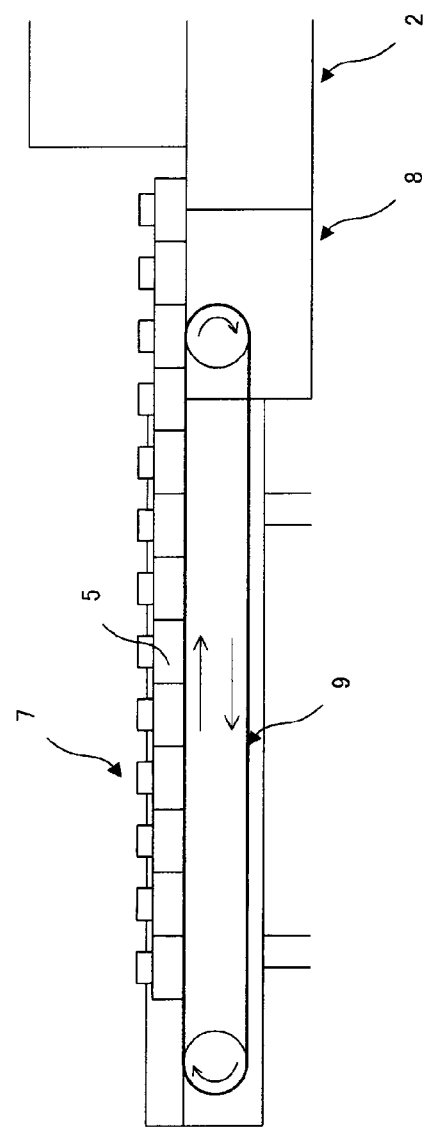
FIG. 15 is a view of a pack cartridge for a system for inspecting an article to be conveyed of another embodiment.

FIG. 15 is a view of a pack cartridge for the system for inspecting an article to be conveyed of another embodiment.

Instead of the bottom plate 71 depicted in FIG. 12, a belt conveyor 9 is used for the pack cartridge 7 for the system for inspecting an article to be conveyed 100 of the other embodiment as depicted in FIG. 15. The belt conveyor 9 is driven to convey the packs 5 toward the specified rotor section 2 via an adapter 8.

As described above, by using the cartridge 7 that uses the belt conveyor 9, the packs 5 can smoothly be exchanged in the short time period when compared to the cartridge 7 depicted in FIG. 12.

The conveyance system 1 according to this embodiment that has been described so far includes, in the conveyance system 1 for conveying the article to be conveyed 10: the rotor section 2 that has the disc-shaped rotor body 21 rotatable about the first axis O1 and the table 22 integrally rotating at the outer peripheral edge of the rotor body 21; the rotation mechanism 3 that has the rotary drive section 31 mounted in the table 22 and the transmission section 32 for transmitting the rotary drive power for driving the rotary drive section 31; the pack 5 that has the first pack member 51 capable of accommodating the article to be conveyed 10 in the upper side, the second pack member 52 contacting the inner periphery of the first pack member 51 in the vertically movable manner and in the lower portion of which the transmission section 32 is inserted, and the pusher member 53 contacting the inner periphery of the second pack member 52 in the vertically movable manner and on which the article to be conveyed 10 is placed, and that is rotatable about the second axis O2 by the rotation mechanism 3; and the lift mechanism 4 that has the arm 41, the one end of which is supported by the rotor body 21 in the vertically movable manner, and the other end of which is used to place the first pack member 51 thereon and supports the second pack member 52. Thus, it is possible with the simple structure to prevent the contact of the article to be conveyed 10 with the guide or the like.

In addition, in the conveyance system 1 according to this embodiment, the pack 5 can be changed to the first state where at least the portion of the article to be conveyed 10 is inserted in the first pack member 51 and the second state where the arm 41 moves downward, the second pack member 52 and the first pack member 51 thereby move downward, and the article to be conveyed 10 that is placed on the pusher member 53 is projected above the first pack member 51 and the second pack member 52. Thus, the state can be changed in accordance with the situation.

In addition, the conveyance system 1 according to this embodiment includes the cap 6 that rotatably presses the article to be conveyed 10 from above and can move vertically in conjunction with the vertical movement of the article to be conveyed 10. Thus, the article to be conveyed 10 can stably be held.

In addition, in the conveyance system 1 according to this embodiment, the pusher member 53 has the projected section 53b that is radially projected and hangs on the second pack member 52 from above. Thus, the article to be conveyed 10 can further stably be held.

In addition, in the conveyance system 1 according to this embodiment, the second pack member 52 has the stopper section 52c that receives the first pack member 51 from below. Thus, falling of the first pack 51 downward can be prevented.

In addition, in the conveyance system 1 according to this embodiment, the lift mechanism 4 has: the coupling member 42 coupled to the arm 41; the cam follower 43 supported by the coupling member 42; and the non-rotational cam member 44 formed with the cam surface 44a that abuts against the cam follower 43. Thus, the arm 41, the first pack member 51, and the second pack member 52 can be lifted or lowered with the simple structure.

In addition, in the conveyance system according to the embodiment of the invention, the transmission section has: the first transmission section on which the pusher is placed and that can rotate and move in the vertical direction; and the second transmission section that can only rotate, and the rotation mechanism has the vertical drive section that drives the first transmission section in the vertical direction. Thus, the pusher can move in the vertical direction.

In addition, in the conveyance system 1 according to this embodiment, the pack 5 can be changed to the third state where the pusher member 53 moves downward by the vertical drive section 33 and the article to be conveyed 10 is placed on the second pack member 52 and the pusher member 53. Thus, the article to be conveyed 10 can stably be held and can rotate at the high speed.

In addition, the system for inspecting an article to be conveyed 100 according to this embodiment includes: the supply section 101 for supplying the article to be conveyed 10; the supply rotor A1 for placing the article to be conveyed 10 that is supplied from the supply section 101 on the pack 5; the conveyance systems 1, C1, C2, C3 for conveying the article to be conveyed 10 that has been supplied from the supply rotor A1 and placed on the pack 5; the imaging devices 111, 112, 113, each of which takes the image of the article to be conveyed 10 on the pack 5; and the inspecting section 122 for inspecting the article to be conveyed 10 from the image taken by each of the imaging devices 111, 112, 113. Thus, the article to be conveyed 10 can accurately be inspected.

In addition, in the system for inspecting an article to be conveyed 100 according to this embodiment, the pack 5 is brought into the second state or the third state at the position where it opposes the imaging device 111a. Thus, the article to be conveyed 10 can further accurately be inspected.

In addition, the system for inspecting an article to be conveyed 100 according to this embodiment has: the pack cartridge 7, in which the packs 5 are aligned; and the pack supply rotors A1, 102, to which the packs are supplied from the pack cartridge 7. Thus, the packs 5 can promptly be supplied in a manner to correspond to the article to be conveyed 10 in the different shape.

In addition, in the system for inspecting an article to be conveyed according to this embodiment, the pack cartridge 7 has the belt conveyor 9 for conveying the packs 5. Thus, the packs 5 can further promptly be supplied.

The description has been made so far on various embodiments of the invention; however, the invention is not limited to these embodiments, and embodiments in such a configuration that the configuration of each of the embodiments is appropriately changed therefor and in such a configuration that the configurations of the embodiments are appropriately combined are also included in the invention unless otherwise departing from the scope of the invention.

REFERENCE SIGNS LIST

1: conveyance system
2: rotor section
21: rotor body
22: table
3: rotation mechanism
31: rotary drive section
32: transmission section
4: lift mechanism
41: arm
42: coupling member
43: cam follower
44: cam member
5: pack
51: first pack member
52: second pack member
53: pusher member
6: cap
7: cartridge
8: adapter
9: belt conveyor
10: article to be conveyed
100: system for inspecting an article to be conveyed

The invention claimed is:

1. A conveyance system for conveying an article to be conveyed, the conveyance system comprising:
a rotor section having a disc-shaped rotor body that is rotatable about a first axis and a table that integrally rotates at an outer peripheral edge of the rotor body;
a rotation mechanism having a rotary drive section that is mounted in the table and a transmission section that transmits rotary drive power for driving the rotary drive section;
a pack having a first pack member configured to accommodate the article to be conveyed in an upper portion, a second pack member that contacts an inner periphery of the first pack member in a vertically movable manner and in a lower portion of which the transmission section is inserted, and a pusher member that contacts an inner periphery of the second pack member in a vertically movable manner and on which the article to be conveyed is placed, and being rotatable about a second axis by the rotation mechanism; and
a lift mechanism having an arm, one end of which is supported by the rotor body in the vertically movable manner, and an other end of which is used to place the first pack member thereon and supports the second pack member.

2. The conveyance system according to claim 1 characterized in that
the pack is configured to be changed to
a first state where at least a portion of the article to be conveyed is inserted in the first pack member, and
a second state where the arm moves downward, the second pack member and the first pack member thereby move downward, and the article to be conveyed that is placed on the pusher member is projected above the first pack member and the second pack member.

3. The conveyance system according to claim 1 further comprising:
a cap that presses the article to be conveyed from above in a manner to allow rotation thereof and that can move vertically in conjunction with vertical movement of the article to be conveyed.

4. The conveyance system according to claim 1 characterized in that
the pusher member has a projected section that is radially projected and hangs on the second pack member from above.

5. The conveyance system according to claim 1 characterized in that
the second pack member has a stopper section that receives the first pack member from below.

6. The conveyance system according to claim 1 characterized in that
the lift mechanism has: a coupling member coupled to the arm; a cam follower supported by the coupling member; and a non-rotational cam member formed with a cam surface that abuts against the cam follower.

7. The conveyance system according to claim 1 characterized in that
the transmission section has: a first transmission section on which the pusher is placed and that can rotate and move in a vertical direction; and a second transmission section that can only rotate, and
the rotation mechanism has a vertical drive section that causes the first transmission section to move in the vertical direction.

8. The conveyance system according to claim 2 characterized in that
the pack is configured to be changed to a third state where the pusher member moves downward by the vertical drive section and the article to be conveyed is placed on the second pack member and the pusher member.

9. An inspection system for inspecting an article to be conveyed, the inspection system comprising:
the conveyance system according to claim 8;
a supply section for supplying the article to be conveyed; and
a supply rotor for placing the article to be conveyed supplied from the supply section on the pack;
wherein the conveyance system conveys the article to be conveyed that has been supplied from the supply rotor and placed on the pack; and wherein the inspection system further comprises:
an imaging device for taking an image of the article to be conveyed on the pack; and
an inspecting section for inspecting the article to be conveyed from the image taken by the imaging device.

10. The inspection system according to claim 9 characterized in that
the pack is brought into the second state or the third state at a position where the pack opposes the imaging device.

11. The inspection system according to claim 10 characterized by having:
a pack cartridge in which the packs are aligned; and
a pack supply rotor to which the packs are supplied from the pack cartridge.

12. The inspection system according to claim 11 characterized in that
the pack cartridge has a belt conveyor for conveying the pack.

13. An inspection system for inspecting an article to be conveyed, the inspection system comprising:
the conveyance system according to claim 1;
a supply section for supplying the article to be conveyed; and
a supply rotor for placing the article to be conveyed supplied from the supply section on the pack;
wherein the conveyance system conveys the article to be conveyed that has been supplied from the supply rotor and placed on the pack; and wherein the inspection system further comprises:
an imaging device for taking an image of the article to be conveyed on the pack; and
an inspecting section for inspecting the article to be conveyed from the image taken by the imaging device.

* * * * *